US00PP26726P2

(12) United States Plant Patent
van Noort

(10) Patent No.: US PP26,726 P2
(45) Date of Patent: May 10, 2016

(54) ***GERANIUM* PLANT NAMED 'NOORTNIGHT'**

(50) Latin Name: *Geranium cinereum*
Varietal Denomination: Noortnight

(71) Applicant: Marco van Noort, Warmond (NL)

(72) Inventor: Marco van Noort, Warmond (NL)

(73) Assignee: Marco van Noort Breeding BV, Warmond (NL)

( * ) Notice: Subject to any disclaimer, the term of this patent is extended or adjusted under 35 U.S.C. 154(b) by 8 days.

(21) Appl. No.: 14/544,143

(22) Filed: Dec. 2, 2014

(51) Int. Cl.
*A01H 5/02* (2006.01)

(52) U.S. Cl.
USPC ..... Plt./324

(58) Field of Classification Search
USPC ..... Plt./324
CPC ..... A01H 5/02; A01H 5/0277
See application file for complete search history.

*Primary Examiner* — Kent L Bell
(74) *Attorney, Agent, or Firm* — Penny J. Aguirre

(57) ABSTRACT

A new cultivar of *Geranium cinereum*, 'Noortnight', that is characterized by its flowers that are clear purple in color with conspicuous dark centers, its floriferous bloom habit with flowers that are consistent in color throughout the plant, and its greater resistance to soil fungi relative to other *Geranium cinereum* cultivars.

2 Drawing Sheets

Botanical classification: *Geranium cinereum.*
Cultivar designation: 'Noortnight'.

BACKGROUND OF THE INVENTION

The present invention relates to a new and distinct cultivar of *Geranium* plant, botanically known as *Geranium cinereum* 'Noortnight' and will be referred to hereafter by its cultivar name, 'Noortnight'.

'Noortnight' was derived from a breeding program conducted by the Inventor in Warmond, The Netherlands. The objectives of the breeding program were to develop new cultivars of *Geranium cinereum* in a range of flower colors that commence bloom early in the season and exhibit disease resistance, compact plant habits and rain resistance. 'Noortnight' arose from a cross made in summer of 2010 between an unnamed and unpatented plant of *Geranium cinereum* from the Inventor's breeding program as the female parent and an unnamed and unpatented plant of *Geranium cinereum* var. *subcaulescens* from the Inventor's breeding program as the male parent. The Inventor selected 'Noortnight' as a single unique plant amongst the seedlings that resulted from the above cross in May of 2012.

Asexual reproduction of the new cultivar was first accomplished by in vitro propagation by the Inventor in Otrebusy, Poland in April of 2014. Asexual propagation by in vitro propagation and root cuttings has determined that the characteristics of the new cultivar are stable and are reproduced true to type in successive generations.

SUMMARY OF THE INVENTION

The following traits have been repeatedly observed and represent the characteristics of 'Noortnight'. These attributes in combination distinguish 'Noortnight' as a new and distinct cultivar of *Geranium.*

1. 'Noortnight' exhibits flowers that are clear purple in color with conspicuous dark centers.
2. 'Noortnight' exhibits a floriferous bloom habit.

3. 'Noortnight' exhibits greater resistance to soil fungi relative to other *Geranium cinereum* cultivars.
4. 'Noortnight' exhibits flowers that are consistent in color throughout the plant.

Both the female and male parent plants of 'Noortnight' differ from 'Noortnight' in having a less floriferous bloom habit and in having flowers with less conspicuously colored centers. 'Noortnight' can also be compared to the *Geranium cinereum* cultivars, 'Laurence Flatman' (not patented) and 'Giuseppii' (not patented). Both cultivars differ from 'Noortnight' in being less floriferous and in having flowers with less conspicuously colored centers.

BRIEF DESCRIPTION OF THE DRAWINGS

The accompanying colored photographs illustrate the overall appearance and distinct characteristics of the new *Geranium*. The photographs were taken of a one year-old plant of 'Noortnight' as field grown in Warmond, The Netherlands and placed in a container for the photographs.

The photograph in FIG. 1 provides an overall view of a plant of 'Noortnight' in bloom.

Figure 1:
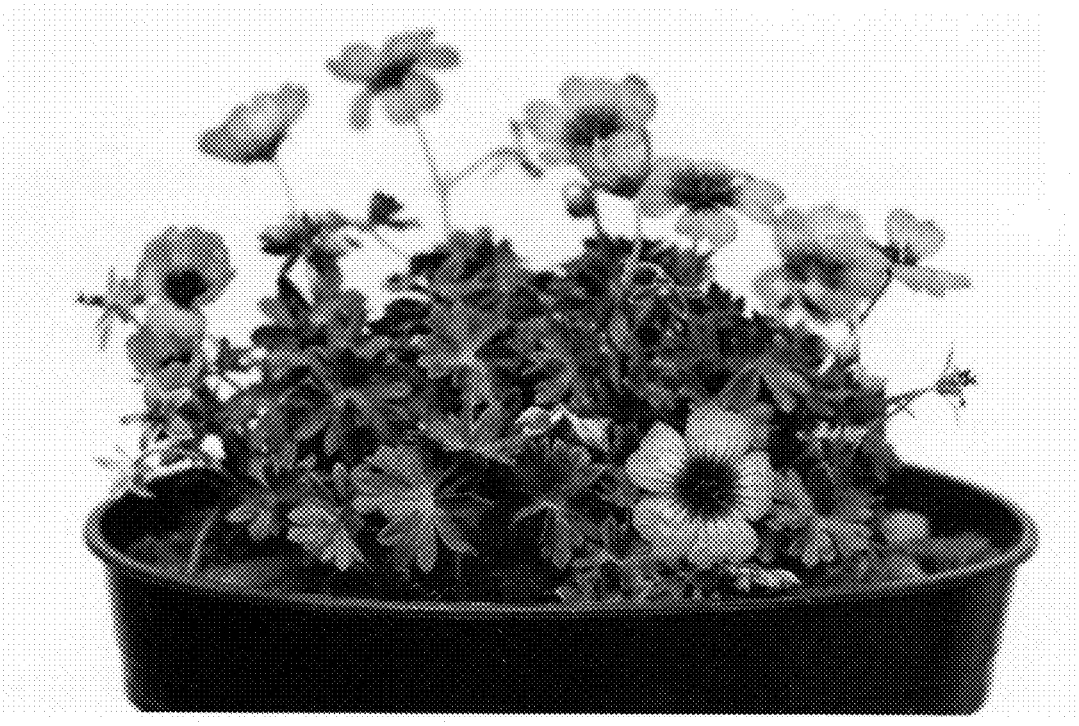
Figure 2:
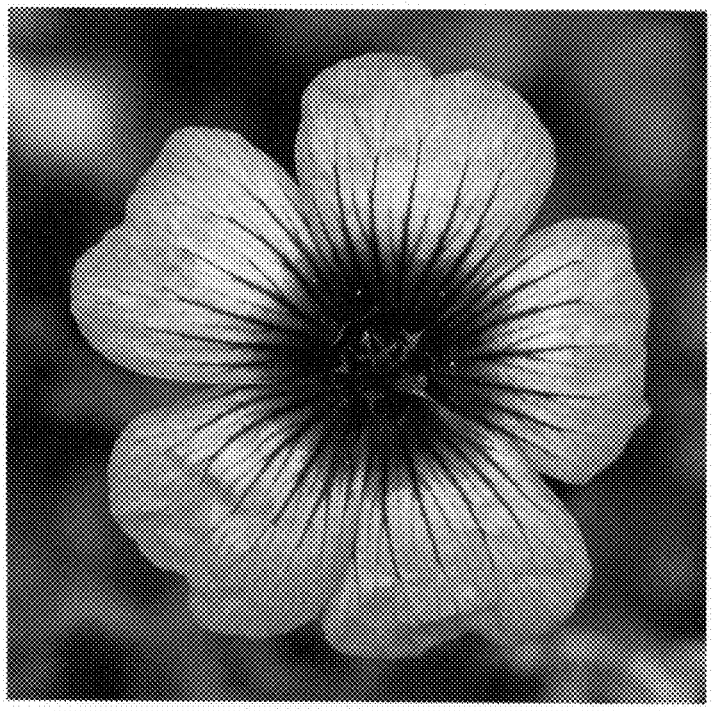

The photograph in FIG. 2 provides a close-up view of the flowers of 'Noortnight'.

Figure 3:
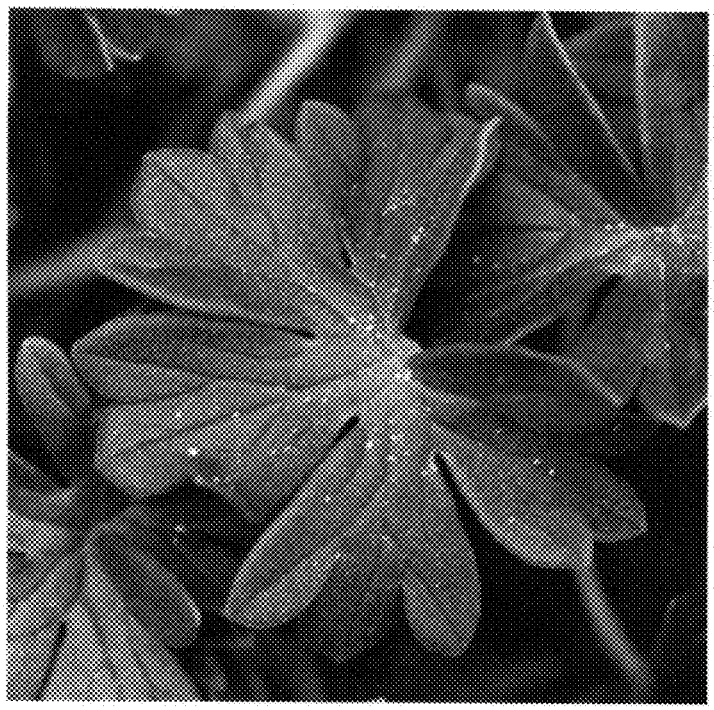

The photograph in FIG. 3 provides a close-up view of the foliage of 'Noortnight'.

The colors in the photographs are as close as possible with the digital photography techniques available, the color values cited in the detailed botanical description accurately describe the colors of the new *Geranium.*

DETAILED BOTANICAL DESCRIPTION OF THE PLANT

The following is a detailed description of one year-old plants of the new cultivar as grown outdoors in Warmond, The Netherlands. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General characteristics:

*Blooming period*.—April into June in The Netherlands.

*Plant habit*.—Low growing, spreading, and flattened with flowers held above the foliage.

*Height and spread*.—An average of 15 cm in height and 25 cm in spread.

*Cold hardiness*.—At least to U.S.D.A. Zone 5.

*Diseases*.—Observed to have some resistance to soil fungi caused by *Botrytis cinerea* and *Pythium* spp.

*Root description*.—Fibrous and fine, primarily 176A in color.

*Root development*.—An average of 20 weeks to fully develop from a rooted cutting in a 9-cm container.

*Growth rate*.—Moderate, an average of 8 cm per month in spring.

*Propagation*.—In vitro propagation (preferred) and root cuttings.

Stem description:

*Stem size*.—Average of 6.2 cm in length and 2 mm in width.

*Stem shape*.—Round.

*Stem color*.—145B, upper surface (sun exposed) tinged 182B TO 182C.

*Stem surface*.—Slightly glossy with stems moderately covered with very short soft adpressed hairs; average of 0.3 mm in length and too small to measure color.

*Stem strength*.—Moderately strong.

*Internode length*.—Average of 1.7 cm.

*Branching*.—Moderately branched with an average of 14 lateral branches.

Foliage description:

*Leaf shape*.—Reniform (in outline), palmately deeply cleft to parted with an average of five lobes.

*Leaf division*.—Simple.

*Leaf base*.—Hastate (touching, not overlapping).

*Leaf apex*.—Broadly acute.

*Leaf venation*.—Palmate, color on upper and lower surface 143A.

*Leaf margins*.—Palmately deeply cleft to parted into an average of five lobes, margins of lobes incised.

*Leaf attachment*.—Petiolate.

*Leaf arrangement*.—Opposite.

*Leaf surface*.—Both surfaces slightly glossy and moderately covered with short and soft adpressed hairs; average of 0.5 mm in length and too small to measure color.

*Leaf size*.—Average of 2.3 cm in length and 2.5 cm in width.

*Leaf color*.—Upper surface young and mature; N137A, lower surface young and mature; 138A.

*Leaf quantity*.—Average of 8 leaves per lateral branch.

*Petioles*.—Average of 4.9 cm in length and 1 mm in diameter, surfaces are 144A to 144C on color, surface puberulent.

*Stipules*.—2 leafy stipules are present at the base of the leaves, narrow deltoid in shape, narrow acuminate apex, truncate base, average of 9 mm in length and 3 mm in width, color of both surfaces 145D with apex 145B, both surfaces puberulent.

Flower description:

*Inflorescence type*.—Single, rotate flowers, arranged in pairs at axillary nodes.

*Lastingness of flowers*.—About 7 days on the plant, sepals persistent.

*Flower size*.—Average of 7 mm in height and 2.7 cm in diameter.

*Flower fragrance*.—None.

*Flower number*.—Average of 8 flowers and buds per lateral system and 112 per plant.

*Flower aspect*.—Upright.

*Flower buds*.—Ovate in shape, average of 7 mm in length and up to 4 mm in diameter, 138A in color with veins 137B, surface moderately covered with short soft adpressed hairs; 0.75 mm in length and too small to measure color.

*Corolla features*.—Petals are unfused and arranged in a rotate form, slightly cupped.

*Petal number*.—5.

*Petal shape*.—Obcordate.

*Petal color*.—When opening and fully open upper surface; N78B, slightly tinged N74A towards apex, base N79B, veins ranging between N186A and N186C, when opening lower surface; N78B, base N79C, veins ranging between N186A and N186C, fully open lower surface; ranging between N72C and N74C, base N79C, veins ranging between N186A and N186C.

*Petal surface*.—Both sides very slightly glossy and moderately velvety.

*Petal margins*.—Entire.

*Petal apex*.—Retuse.

*Petal size*.—Average of 1.5 cm in length and 1.2 cm in width.

*Calyx*.—Rotate and cupped, 4 mm in length and 1.3 cm in diameter.

*Sepals*.—5, ovate in shape, average of 7 mm length and 2.5 mm in width, entire margin, mucronate apex, cuneate base, both surfaces are matte, color young upper surface; 137B, color young lower surface; 143B, tip 143A, mature upper surface; 137B, mature lower surface; 143B, tip 143A.

*Peduncles*.—Round in shape, average of 3.6 cm in length and 1.5 mm in diameter, strong, held at a 30° angle to the lateral branch, color of surfaces are 144C, upper surface is strongly tinged 174B, surface puberulent.

*Pedicels*.—Round in shape, average of 1.8 cm in length and 1 mm in diameter, strong, one flower straight on top of peduncle, the second flower held in an average angle of 30° to lateral branch, color of surfaces are 177C, surface puberulent.

Reproductive organs:

*Gynoecium*.—1 pistil, average of 3 mm in length, 5 stigmas are decurrent (reflexed) and N79B to N79C in color, style is an average of 2 mm in length and 153D in color, ovary is 144A in color.

*Androecium*.—10 stamens, anthers are dorsifixed, oblong in shape and held at a 90° angle on top of filament, 1.75 mm in length, and 203B to 203C in color, filaments are 3 mm in length and N79B to N79C in color, pollen is low in quantity and 152D in color.

*Fruit/seeds*.—None detected.

It is claimed:

1. A new and distinct cultivar of *Geranium* plant named 'Noortnight' as herein illustrated and described.

* * * * *